United States Patent [19]

Sherman

[11] Patent Number: 5,282,801
[45] Date of Patent: Feb. 1, 1994

[54] TOP TIGHTENING CLAMP ASSEMBLY FOR A SPINAL FIXATION SYSTEM

[75] Inventor: Michael C. Sherman, Memphis, Tenn.

[73] Assignee: Danek Medical, Inc., Memphis, Tenn.

[21] Appl. No.: 18,800

[22] Filed: Feb. 17, 1993

[51] Int. Cl.⁵ .............................................. A61F 5/02
[52] U.S. Cl. ....................................... 606/61; 606/73; 623/17
[58] Field of Search ........................ 606/60, 61, 72, 73, 606/62, 64; 623/17

[56] References Cited

U.S. PATENT DOCUMENTS

| | | | |
|---|---|---|---|
| 4,987,892 | 1/1991 | Krag et al. | 606/61 |
| 5,053,034 | 10/1991 | Olerud | 606/60 |
| 5,122,131 | 1/1992 | Tsou | 606/61 |
| 5,176,678 | 1/1993 | Tsou | 606/60 |
| 5,209,752 | 3/1993 | Ashman et al. | 606/72 |

FOREIGN PATENT DOCUMENTS

2096465 10/1982 United Kingdom ................. 606/61

Primary Examiner—Peter A. Aschenbrenner
Assistant Examiner—Sonya C. Harris
Attorney, Agent, or Firm—Woodard, Emhardt, Naughton, Moriarty & McNett

[57] ABSTRACT

A spinal fixation system is provided for engagement to the spine of a patient between several vertebral levels, which includes an elongated spinal rod configured for placement adjacent the spine. The system includes a number of vertebral fixation elements, each including a vertebra engaging portion and a rod engaging portion formed by a pair of posts extending from the vertebra engaging portion. The vertebral fixation elements are engaged to the spinal rod each by way of a top-loading clamp that permits access directly from the top of the instrumentation site for tightening the system. In particular, the clamp includes a body defining an elongated bore configured to receive the spinal rod therethrough so that the rod can at least initially slide along the length of the bore. A pair of threaded bores extend from opposite top and bottom surfaces of the body, each intersecting the elongated rod bore. The clamp further includes a projection extending from the body terminating in a T-bar arranged generally parallel to the longitudinal axis of the spinal rod. The T-bar includes a clamping surface directed inwardly toward the elongated bore that is configured to engage the pair of posts of the vertebral fixation element. A set screw is provided that is threaded into one of the threaded bore bearing against the spinal rod disposed within the rod bore, so that the set screw clamps the rod and the posts of the vertebral fixation element against the T-bar.

17 Claims, 3 Drawing Sheets

TOP TIGHTENING CLAMP ASSEMBLY FOR A SPINAL FIXATION SYSTEM

BACKGROUND OF THE INVENTION

The present invention concerns spinal fixation systems, and particularly systems utilizing elongated rods adjacent the spinous process providing a base for connecting fixation elements to several vertebral levels. More specifically, the invention concerns improvements to the manner in which the vertebral fixation elements are engaged to the elongated spinal rod.

Several techniques and systems have been developed for correcting and stabilizing spinal curves and facilitating spinal fusion. In one system, a bendable rod is longitudinally disposed adjacent the vertebral column, or spinous process, and is fixed to various vertebrae along the length of the column by way of a number of fixation elements. A variety of fixation elements can be provided which are configured to engage specific portions of the vertebra. For instance, one such fixation element is a spinal compression/distraction hook. This type of spinal hook is used to anchor the rod by engaging the laminae of the vertebra. Another fixation element is a spinal screw, which includes cancellous threads for engagement within the pedicle of a vertebra.

An example of a rod-type spinal fixation system under consideration with the present invention is the TSRH ® spinal system sold by Danek Medical, Inc. In this system, a spinal hook, such as the hook H shown in FIG. 1 for example, is engaged to an elongated fixation rod R by way of an eyebolt assembly E. As is known in the art, the eyebolt E is mounted on the spinal rod and captured within yokes on the spinal hook. A nut N is then threaded onto a threaded post of the eyebolt to clamp the hook yoke between the nut and the fixation rod R. In this manner, the eyebolt E and the yokes of the hook H provide three degrees of fixation as represented by the arrows in FIG. 1. Details of the TSRH ® spinal implant system are disclosed in the "TSRH ® Surgical Technique Manual provided by Danek Medical, Inc., published in 1990, which disclosure is incorporated herein by reference.

Figures 1, 2:
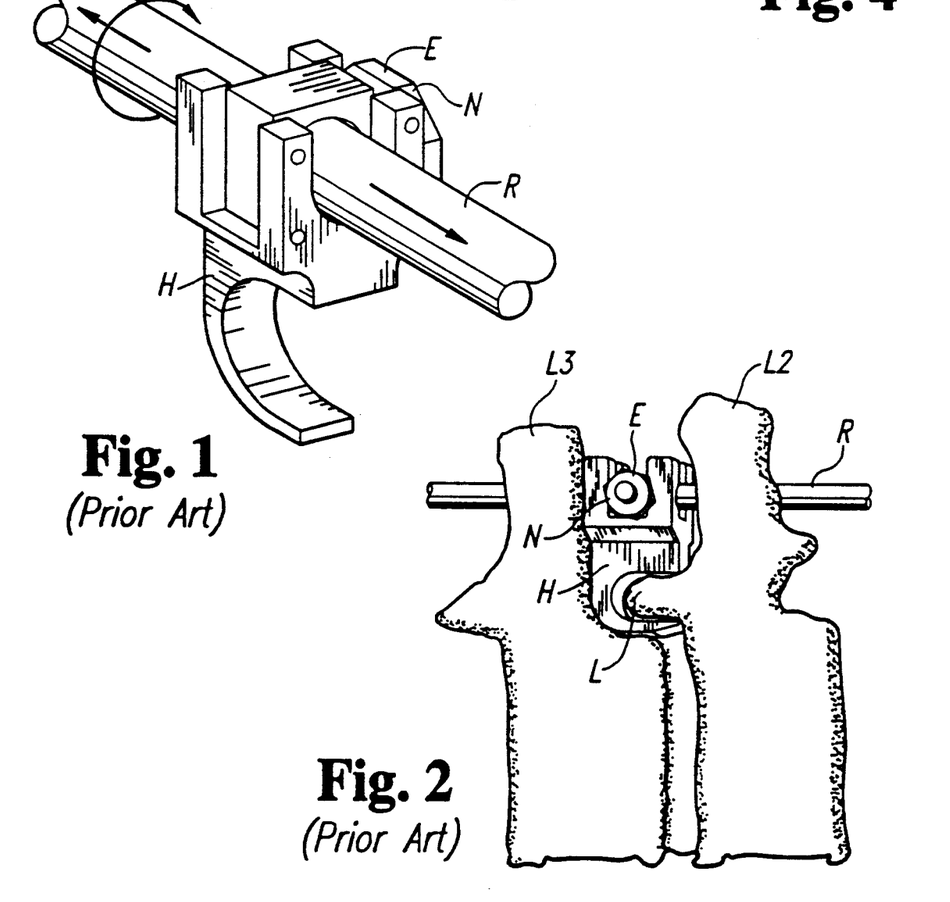
FIG. 1 shows a spinal hook of known design engaged to a fixation rod by way of an eyebolt assembly, as configured in accordance with one prior art system, the TSRH ® spinal system.
FIG. 2 is a side view showing the system depicted in FIG. 1 in which a standard hook is engaged about the laminae of a lumbar vertebra.

It is the goal of the surgeon using spinal implant systems such as the Danek TSRH ® system to apply vertebral fixation elements, such as a spinal hook or a bone screw, to the spine in appropriate anatomic positions, and then to engage each fixation element to the spinal rod. One problem with the spinal hooks H of the prior art, as represented in FIGS. 1 and 2, is that the hooks are rather bulky and wide since the fixation yokes of the hook were configured to surround the spinal rod R. Moreover it had been found that hooks such as hook H only allow the rod to be implanted in one position relative to the spinal column as dictated by the required position of the shoe of the hook against the vertebra.

Figure 3:
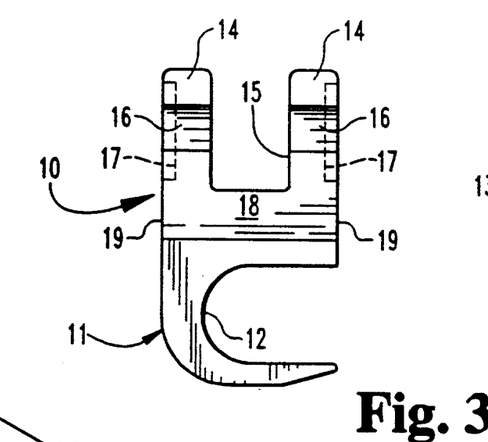
FIG. 3 is a side elevational view of the spinal hook of recent design for which the top-tightening clamp assembly of the present invention is adapted to engage.
Figure 4:
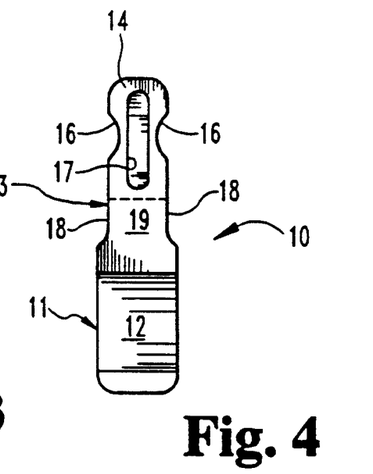
FIG. 4 is an end elevational view of the spinal hook shown in FIG. 3.

In order to address that and other problems with the prior art systems shown in FIGS. 1 and 2, new spinal fixation elements have been developed which are the subject of pending applications assigned to the assignee of the present invention. One such fixation element, a spinal hook 10, is shown in FIGS. 3 and 4, includes a shoe 11 having a bone engaging surface 12. The bone engaging surface 12 can be formed in any known shape to engage a laminae of a vertebra, for instance. Integral with the shoe 11 is a top portion 15 that forms a pair of posts 14 disposed apart from each other in the form of a U-shaped yoke to define a slot 15 therebetween. The slot 15 is wide enough to receive an eyebolt assembly, such as eyebolt assembly E shown in FIGS. 1 and 2. A pair of coaxial grooves 16 formed in each lateral surface 18 of the hook 10 are each configured to receive a portion of a spinal rod, such as rod R shown in FIGS. 1 and 2. These rod grooves 16 are present on each lateral surface 18 of the posts 14 so that the hook 10 can be oriented on either side of a spinal rod. Slots 17 are provided on each end face 19 for engagement by a hook-holding insertion instrument.

Figures 9, 10:
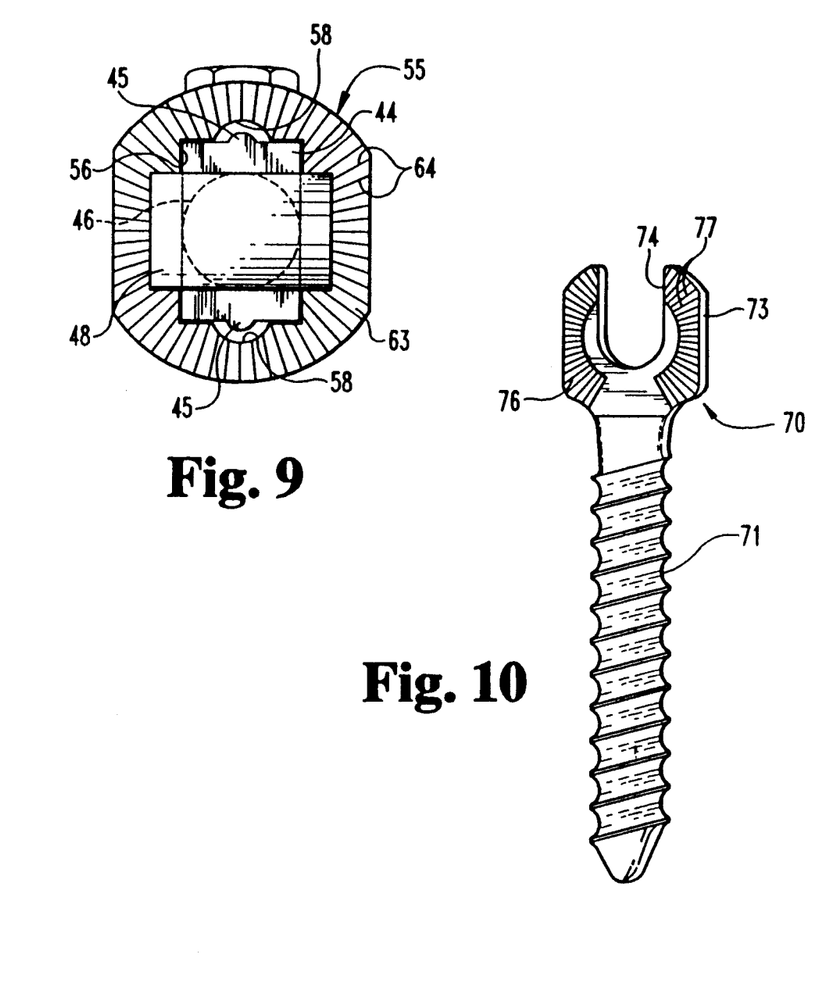
FIG. 9 is a side elevational view of the alternative embodiment shown in FIG. 8.
FIG. 10 shows a variable angle spinal screw for use with the top-tightening clamp assembly depicted in FIGS. 8 and 9.

Another newly developed vertebral fixation element is a variable angle spinal screw, which is the subject of a pending application assigned to the assignee of the present invention. Certain details of this novel variable angle screw system is shown in FIG. 10. In particular, the screw 70 includes a shank 71 having bone engaging or cancellous threads formed thereon. The screw 70 also includes an upper yoke 73 formed by a pair of posts which define a U-shaped slot opening 74 configured to engage a specially designed connector for connecting the screw 70 to a spinal rod. The screw 70 includes an interdigitating face 76 having a number of radial splines 77 formed thereon.

Leaving the details of these newly developed vertebral fixation elements to their respective pending applications, it can be appreciated that the central post hook 10, of FIGS. 3 and 4, and the variable angle screw 70, of FIG. 10, have increased the versatility of rod-type spinal implant systems, such as the TRSH ® system provided by Danek Medical. However, one feature consistent between these newly developed fixation systems, as well as the prior art spinal hook H shown in FIG. 1, is that the eyebolt assembly E used to engage the fixation component to the spinal rod is "side-tightening". In other words, the threaded post of the eyebolt E and the nut N engaging the post both project laterally away from the spinal rod R, as specifically depicted in FIGS. 1 and 2. It has been found in practice that it is often cumbersome to get engage the nut N with a wrench to tighten the nut onto the eyebolt assembly E. Moreover, simple mechanics dictates that the wrench can only be moved through a partial turn before the handle of the wrench contacts the surrounding tissue. This necessitates taking the wrench off of the nut and re-engaging it for an additional partial rotation. Ratchet type wrench systems are typically not acceptable in procedures of this sort because the lateral space required for the ratchet mechanism unnecessarily impinges on the surrounding tissue and requires greater space at the surgical site.

Spinal and orthopaedic procedures are rapidly becoming prevalent surgeries, largely because of the high incidence of low back pain syndrome. In the past, surgical techniques for alleviating low back pain or for addressing spinal deformities or injuries has required fairly complicated and massive surgical techniques. The focus in recent times has been to greatly reduce the degree of invasion into the patient required for instrumenting a spine, as well as to reduce the amount of trauma to tissue surrounding the instrumentation, both during the procedure and after the spinal instrumentation has been implanted.

One cog in this worthwhile goal for minimally invasive spinal surgical techniques, is to provide an improved means for clamping the various vertebral fixation components to a spinal rod in situ. Such a system should eliminate the side-tightening requirement of prior art systems. In addition, such a system should retain the versatility achieved by newly developed central post hooks and variable angle screw fixation elements. It is the goal of the present invention to address this and other concerns.

SUMMARY OF THE INVENTION

The present invention contemplates a spinal fixation system for engagement to the spine of a patient between several vertebral levels, particularly utilizing an elongated spinal rod configured for placement adjacent the spine. The system includes a number of vertebral fixation elements, each including a vertebra engaging portion and a rod engaging portion. In accordance with the invention, the rod engaging portions are of the type having a pair of posts extending from the vertebra engaging portion, the posts defining a slot opening therebetween. Opposite lateral surfaces of the posts are configured to engage the spinal rod, particularly by way of coaxial grooves formed in each lateral surface. A top-loading clamp is provided for clamping the vertebral fixation element to the spinal rod to permit top tightening of the clamp onto the rod. The clamp includes a body defining an elongated bore configured to receive the spinal rod therethrough, and having a length along its longitudinal axis greater than the diameter of the spinal rod so that the rod can at least initially slide within the bore. The body further defines first and second threaded bores extending from opposite top and bottom surfaces of the body, both which intersect the elongated bore. A set screw is provided which can alternatively be threaded through either of the threaded bores and into the rod bore to bear against the spinal rod disposed within.

The top-loading clamp further includes a projection extending from the body generally parallel to the longitudinal axis of the elongated bore. The projection terminates in a T-bar which is arranged generally parallel to the longitudinal axis of the spinal rod when the rod extends through the elongated bore. The T-bar has a clamping surface directed inwardly toward the elongated bore that is configured to engage the lateral surfaces of each of the pair of posts of the vertebral fixation element.

The top-loading clamp provides means for clamping the posts of the vertebral fixation element to the spinal rod. Specifically, both the rod and the fixation element are clamped between the set screw and the clamping surface of the T-bar as the set screw is threaded further into the rod bore. The clamp of the present invention provides this means for clamping the components together while permitting top-tightening of the system, that is directly above the instrumentation site rather than laterally relative to the spinal rod.

In one embodiment, the vertebral fixation element is a spinal hook. In another embodiment, the fixation element is a variable angle screw having radial splines on one face of the rod engaging portion of the screw. In this embodiment, the top-loading clamp includes a washer having a first surface configured to engage the spinal rod, and an opposite second surface which includes a plurality of radial splines adapted for interdigitating engagement with the radial splines of the variable angle screw. The washer includes an opening therethrough configured to permit insertion of the washer over the T-bar. The washer is slidably mounted over a hub of the body, which is staked to keep the washer from sliding off the hub. In this embodiment, the washer is disposed between the vertebral fixation element and the spinal rod and is clamped therebetween when the set screw bears against the spinal rod. The interdigitating splines prevent rotation of the vertebral fixation element about the projection.

The top-loading clamp of the present invention provides the significant advantage of allowing the clamping mechanism to be tightened from directly above the instrumentation site. Moreover, the two threaded bores allows the clamp to be oriented on either side of a spinal rod, as necessary to mate with a vertebral fixation element already engaged to a vertebra. Other advantages and benefits of the present invention can be discerned from the following written description and accompanying figures.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As discussed in the background of the invention, the present invention in the preferred embodiment, contemplates a clamp assembly adapted to engage a newly developed spinal hook of the type shown in FIGS. 3 and 4, or a newly developed variable angle screw of the type shown in FIG. 10. However, it is understood that other hook and bone screw configurations are contemplated for use with the clamp assembly of this invention.

The clamp assembly of the preferred embodiment is specifically adapted to engage these vertebral fixation elements to an elongated spinal rod.

Figure 5:
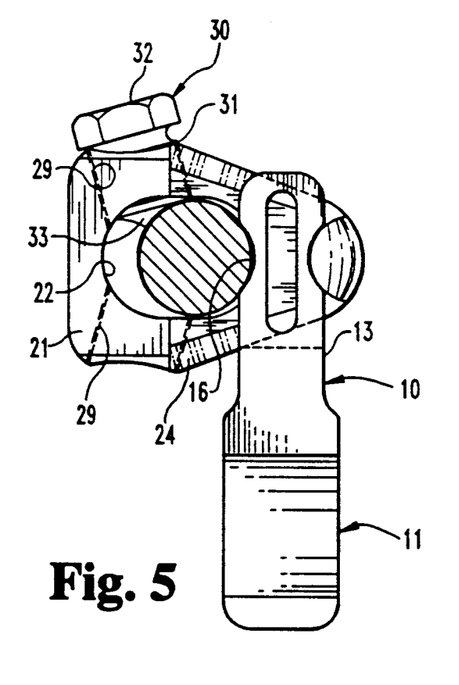
FIG. 5 is an end elevational, partial cross sectional, view of a top-tightening clamp assembly in accordance with one embodiment of the present invention, shown clamping a spinal hook of the type shown in FIG. 4 to a spinal rod.
Figure 6:
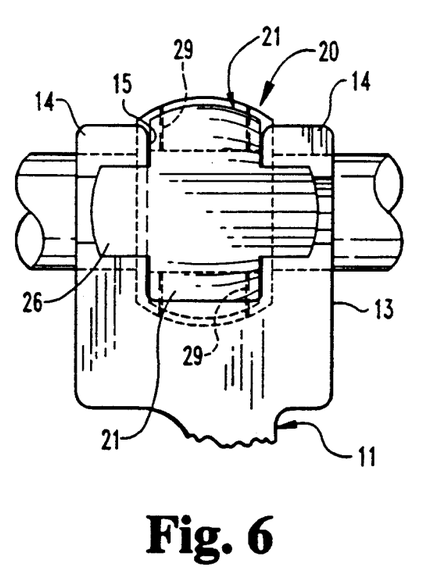
FIG. 6 is a side elevational view of the assembly shown in FIG. 5.
Figure 7:
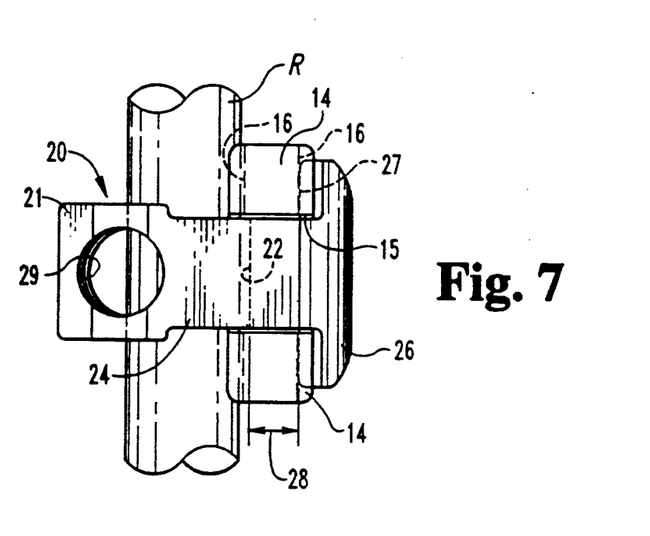
FIG. 7 is a top elevational view of the assembly shown in FIG. 5.

In accordance with one embodiment of the invention, a top-tightening clamp assembly 20 is provided, as shown in FIGS. 5-7. The assembly 20 includes a clamp body 21, which is preferably formed of a biocompatable metal such as titanium or stainless steel. The clamp body 21 defines a rod bore 22 through which a spinal rod, such as rod R, extends. It will be noticed from FIG. 5 that the rod bore 22 is elongated so that the spinal rod R can move, at least initially, within the bore along a longitudinal axis of the bore transverse to the longitudinal axis of the spinal rod R. In one specific embodiment adapted for use with a ¼" spinal rod, the length of the bore along its longitudinal axis is 0.351 inches. The ends of the rod bore are formed at a radius that is slightly larger than the diameter of the spinal rod.

The clamp body 21 includes a projection 24 extending laterally therefrom relative to the spinal rod once the clamp assembly 20 is engaged within the patient. The projection 24 extends generally parallel to the longitudinal axis of the rod bore 22 and terminates in a T-bar 26, so named because the bar 26 combined with the projection 24 are in the shape of a "T", with the T-bar arranged generally parallel to the longitudinal axis of the spinal rod R extending through the rod bore 22. The T-bar includes a inwardly facing surface 27 that is convexly curved toward the rod bore. Reference to the direction "inward" in connection with this invention is intended to mean facing toward the rod bore 22 and the spinal rod R within.

The clamp body 21 is particularly designed so that the distance between the curved inward surface 27 of the T-bar 26 and the closest point of the rod bore 22 is less than the width of a vertebral fixation element to be clamped to the rod. In the preferred embodiment, this fixation element is the central post hook 10 as previously described and as depicted most clearly in FIG. 5. Consequently, the distance, labeled 28 in FIGS. 5 and 7, between the innermost point on the curved inward surface 27 and the nearest point of the rod bore 22 is narrower than the width of the post 14 of the hook 10. In this manner, the spinal rod R can contact the groove 16 on one side of the spinal hook 10, without first striking the end of the rod bore 22. As shown in FIG. 5, the clamp assembly 20 contemplates that the spinal hook 10 will be firmly engaged between a spinal rod R and the inward surface 27 of the T-bar 26. The surface 27 of the T-bar is configured to mate with one of the coaxial grooves 16 in the post 14 of the spinal hook 10. For engaging one specific spinal hook, the distance 28 is 0.110 inches.

The clamp body 21 further defines a pair of threaded bores 29, each projecting inwardly from opposite sides of the body toward the rod bore 22, and in fact intersecting the rod bore. Each of the threaded bores 29 is adapted to receive a set screw 30 threaded therein. The set screw 30 includes a threaded stem 31 having threads for mating with the threads of the bores 29, and a driving head 32 which can assume a variety of configurations. In FIG. 5, the driving head 32 is configured to accept a standard socket wrench, although the driving head 32 can be alternatively configured to receive an allen head wrench. At the distal end of the threaded stem 31 is a contoured tip 33 adapted to engage the surface of a spinal rod R. Preferably, the tip 33 is formed in a spherically conical shape, as depicted in FIG. 5, to provide a line contact with the rod along the curvature of the tip. In one specific embodiment, the tip 33 is formed at a 0.115 inch radius to engage a ¼ inch spinal rod. Alternatively, the tip 33 may also be rounded or blunt, thereby providing essentially a point contact with the spinal rod.

With the spherically conical shaped tip 33, it is preferred that the threaded bore 52 intersect the rod bore 22 at a non-perpendicular angle to the longitudinal axis of the bore. Preferably, this bore 52 intersects the rod bore 22 at an angle between 60° and 90°. In the specific embodiment shown in FIG. 5, the threaded bore 52 intersects the rod bore 22 at an angle of 74.5°. This angle allows a firm contact between the tip 33 of the set screw and the spinal rod R, while also keeping the driving head 32 accessible from the top of the implanted construct.

With the foregoing description accompanied by the FIGS. 5-7, the manner of using the clamp assembly 20 of the present invention may be clear to one of ordinary skill in the art. Specifically, in accordance with known spinal rod instrumentation procedures, a fixation element, such as hook 10 is first positioned in contact with a vertebra to be instrumented. The spinal rod R is then be positioned appropriately to provide purchase for engagement with the hook 10. Alternatively, the spinal rod R can already be positioned rigidly at its ends or at various locations along the rod at several vertebral levels. In this instance, an additional spinal hook would be added subsequent to the positioning of the spinal rod and the clamp assembly 20 would be used to engage the hook to the rod. In either approach, it is important that the clamp assembly 20 already be situated on the spinal rod, that is with the rod R threaded through the rod bore 22, prior to introduction of the rod into the patient. The set screw 30 is initially loosely threaded into one of the threaded bores 29 so that there is adequate free play between the spinal rod and the walls of the bore 22. In addition, the clamp assembly 20 is permitted to slide longitudinally along the length of the spinal rod to the location of the hook to be engaged to the rod.

Once the clamp assembly 20 is positioned adjacent the spinal hook 10, the hook is situated with the opposite posts 14 straddling the projection 24—that is, with the projection 24 extending through the slot 15 in the spinal hook 10, as shown in FIGS. 6 and 7. The clamp assembly 20 can be manipulated so that the curved inward surface 27 of the T-bar 26 engages a groove 16 in one lateral surface 18 of the hook. Once the clamp assembly 20 is properly oriented between the spinal rod R and the fixation hook 10, the set screw 30 is then be tightened within the threaded bore 29 so that the contoured tip 33 contacts and presses the spinal rod R against a groove 16 of the hook 10. Preferably, the set screw 30 is threaded into the bore as far as possible, finger tight. It has been found that this provides adequate engagement to clamp the spinal rod to the fixation element or hook 10 by way of the clamp assembly 20.

The clamp assembly 20, and particularly the clamp body 21 is provided with a pair of opposite threaded bores 29 to increase the versatility of the assembly of the present invention. Since the clamp body 21 must be pre-engaged on the spinal rod, it is possible that the hook to be clamped to the rod will be situated on one side or the other of the rod once the rod has been bent and/or rotated into position. For example, the hook 10 is shown engaged on the right side of the rod R in FIG. 5. However, once the entire spine has been instrumented it can be discovered that the hook will actually reside on the left side of the rod R. In this instance it is absolutely essential that the clamp assembly 20 be capable of altering its orientation to engage the left-side located spinal hook. Consequently, in this instance the clamp body 21 need only be rotated about the spinal rod R so that the T-bar 26 projects to the left of the spinal rod (as viewed in FIG. 5) and what had been the lowermost bore 29 is now facing upward to receive a set screw 30 therein. Most preferably, the clamp body 21 is symmetric about the longitudinal axis of the rod bore 22.

Figure 8:
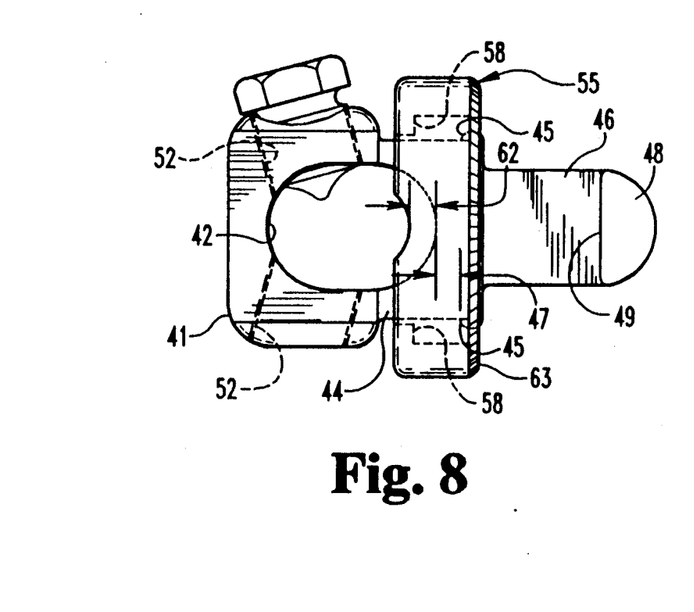
FIG. 8 shows an alternative embodiment of a top-tightening clamp assembly for use with a variable angle screw.

The present invention is also readily adapted for engagement with a variable angle screw, such as the screw 70 depicted in FIG. 10. Specifically, this alternative embodiment of the invention is shown in FIGS. 8 and 9. It is understood of course that this alternative embodiment is configured to engage a spinal rod just as the embodiment shown in FIGS. 5-7. However, for clarity the spinal rod and the specific location of the variable angle screw has been omitted from the figures.

In the alternative embodiment of FIGS. 8 and 9, a clamp assembly 40 includes a clamp body 41 which defines a rod bore 42, which is for all intents substantially identical to the same features on the clamp body 21 in FIG. 5. However, in a modification from the previous embodiment, the clamp body 41 defines a hub 44, from which a circular projection 46 extends. The hub 44 in the preferred embodiment is generally rectangular in shape, as shown in FIG. 9. A T-bar 48 is formed at the end of the projection 46. In a further modification from the previous embodiment, the T-bar 48 does not include a curved inward surface, but instead has a flat inward surface 49 facing toward the rod bore 42. As with the previous embodiment, the clamp body 41 defines opposite threaded inwardly opening bores 52 which are adapted to set screws 53.

The clamp assembly 40 further includes an interdigitating washer 55. The washer 55 includes an opening 56 which is configured similar to the hub 44 both dimensionally and in its shape. The opening 56 and the hub 44 have almost identical dimensions so that the washer 55 can be passed onto the hub 44. In order to facilitate retaining the washer 55 on the hub, the washer includes a pair of staking recesses 58 shown in FIG. 8 and 9. The staking recesses 58 receive each receive a staked portion 45 of the hub 44 so that the washer cannot slide off the hub. A staking tool can be used to depress the hub 44 to form the staked portions 45 when the washer is situated on the hub. It is understood that this staking operation is done prior to implanting the assembly 40 within the patient, or engaging it onto the spinal rod.

In order to allow the washer 55 to be received on the hub, it is important that the T-bar 48 be similarly shaped but slightly smaller than the opening 56 in the washer. The washer 55 can then be passed over the T-bar 48 and rotated so that the opening 56 is oriented perpendicular to the axis of the T-bar 48, as shown in FIG. 9.

Once staked onto the hub 44, the washer 55 can slide along the hub between the body 41 and the staked portions 45. It is contemplated that the free-play of the washer at its thinnest point on the rod groove 61 and the staking recesses 58 (denoted 62 in FIG. 8), is greater than the distance between the end of the rod bore 42 and the staked portions 45 (denoted 47 in FIG. 8). This dimensional relationship ensures that the spinal rod has room to engage the rod groove 61 of the washer 55 before contacting the end of the rod bore 42 when clamped by the set screw 53.

In one important feature of this embodiment, the washer 55 includes a rod face 60 which is directed toward the rod bore 42. The rod face 60 defines a groove 61 for receiving a spinal rod therein, in the manner shown in FIG. 5. The washer 55 further includes an opposite outward face 63 which incorporates the interdigitating feature of the invention. Specifically, the outward face 63 includes several radial splines 64 formed thereon. These radial splines are configured comparably with the radial splines 77 on the variable angle screw 70. The projection 46 is circular in cross section so that the variable angle screw 70 can be rotated relative to the projection about its U shaped slot 74. Thus, the clamp assembly 40 of this embodiment is well suited for receiving a variable angle screw 70 that is engaged into the pedicle of the vertebra, for instance, at a non-vertical angle (that is angled in the plane of the spinous process).

It can be appreciated from the description of the preferred embodiments that this invention provides novel means for clamping various spinal fixation elements to an elongated spinal rod. The clamp assemblies 20 and 40 in accordance with this invention exhibit great versatility in making the connection between the fixation element and the spinal rod. Perhaps most significantly, the clamp assemblies in accordance with the invention allow for top-tightening of the engagement between the spinal rod and the fixation element. In the case of the clamp assembly 20, a spinal hook can be tightened against a spinal rod by way of a top-tightening set screw 30 which presses against the spinal rod. In the clamp assembly 40, the top-tightening set screw 53 pushes against a spinal rod within the bore 42, which pushes against the washer 55, which finally presses the upper yoke 73 of a variable angle screw 70 between the spline face 63 and the inward face 49 of the T-bar 48.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal fixation system for engagement to the spine of a patient between several vertebral levels, comprising:

an elongated spinal rod configured for placement adjacent the spine of a patient spanning several vertebral levels, said rod defining a longitudinal rod axis along its length;

a vertebral fixation element including;

a vertebra engaging portion; and         a rod engaging portion formed by a pair of posts extending from said vertebra engaging portion, said posts defining a shot opening therebetween and said posts each having opposite lateral surfaces configured to engage said spinal rod; and     a top-loading clamp for clamping said vertebral fixation element to said spinal rod, including;

a body defining an elongated bore configured to receive said spinal rod therethrough, said elongated bore having a length along its longitudinal axis greater than the diameter of said spinal rod so that said rod can at least initially slide within said bore;

said body having a top surface and defining a first threaded bore therethrough from said top surface and intersecting said elongated bore; therethrough from said top surface and intersecting said elongated bore;

a projection extending from said body generally parallel to the longitudinal axis of said elongated bore, said projection terminating in a T-bar arranged generally parallel to the longitudinal axis of said spinal rod when said rod extends through said elongated bore, said T-bar having a clamping surface directed inwardly toward said elongated bore, said clamping surface configured to engage one of said opposite lateral surfaces of each of said pair of posts of said vertebral fixation element; and a set screw threaded for engagement through said first threaded bore, said set screw having a tip configured for bearing against said spinal rod when said rod extends through said elongated bore;

wherein said posts of said vertebral fixation element are disposed between said clamping surface of said T-bar and said spinal rod when said rod extends through said elongated bore, with said projection extending through said slot opening, and further wherein said spinal rod and said posts of said vertebral fixation element are clamped between said clamping surface of said T-bar and said tip of said set screw when said set screw is threaded through said first threaded bore into said elongated bore with said tip bearing against said spinal rod.

2. The spinal fixation system of claim 1, wherein:

each of said opposite lateral surfaces, of each of said pair of posts of said vertebral element, defines a coaxial groove configured to receive said spinal rod therein; and said clamping surface of said T-bar is curved to be received within said coaxial groove.

3. The spinal fixation system of claim 1, wherein:

said pair of posts of said vertebral fixation element has a thickness between said opposite lateral surfaces; and said top-loading clamp defines a length between said elongated bore and said clamping surface of said T-bar, said length being less than said thickness of said pair of posts.

4. The spinal fixation system of claim 1, wherein:

said body includes a bottom surface opposite said top surface and further defines a second threaded bore therethrough from said bottom surface intersecting said elongated bore, whereby said set screw can be threaded alternatively into said first threaded bore or said second threaded bore to clamp said spinal rod within said elongated bore.

5. The spinal fixation system of claim 4, wherein said body is symmetric about a plane including the longitudinal axis of said rod bore.

6. The spinal fixation system of claim 1, wherein said first threaded bore intersects said rod bore at an angle between 60° and 90°.

7. The spinal fixation system of claim 1, wherein:

at least one of said opposing lateral surfaces, of each of said pair of posts includes a plurality of radial splines; and said top-loading clamp includes;

a washer having a first surface configured to engage said spinal rod, and an opposite second surface which includes a plurality of radial splines adapted for interdigitating engagement with the radial splines of said pair of posts, said washer further defining an opening therethrough configured to permit insertion of said washer over said T-bar; and means for slidably engaging said washer to said body adjacent said rod bore, wherein said washer is disposed between said vertebral fixation element and said spinal rod and is clamped therebetween when said set screw bears against said spinal rod, whereby the interdigitating radial splines of said pair of posts and said washer prevent rotation of said vertebral fixation element about said projection.

8. The spinal fixation system of claim 7, wherein:

said body defines a hub between said rod bore and said projection, said hub having a shape complementary to said opening in said washer to prevent rotation of said washer about said hub when said washer is disposed thereon; and said means for slidably engaging said washer includes means for mounting said washer on said hub to permit sliding of said washer in a direction parallel to the longitudinal axis of said rod bore.

9. The spinal fixation system of claim 8, wherein said means for mounting includes:

at least one staking recess defined in said first surface integral with said opening; and a staked portion of said hub projecting outward therefrom for engagement within said staking recess when said washer is disposed on said hub.

10. A top-loading clamp for clamping a vertebral fixation element to a spinal rod, comprising:

a body defining an elongated bore configured to receive a spinal rod therethrough, said elongated bore having a length along its longitudinal axis greater than the diameter of the spinal rod so that the rod can at least initially slide within said bore;

said body having a top surface and defining a first threaded bore therethrough from said top surface and intersecting said elongated bore;

a projection extending from said body generally parallel to the longitudinal axis of said elongated bore, said projection terminating in a T-bar arranged generally parallel to the longitudinal axis of the spinal rod when the rod extends through said elongated bore, said T-bar having a clamping surface directed inwardly toward said elongated bore, said clamping surface configured to engage a surface of a vertebral fixation element disposed between the spinal rod and said T-bar; and a set screw threaded for engagement through said first threaded bore, said set screw having a tip configured for bearing against the spinal rod when the rod extends through said elongated bore, wherein the spinal rod and the vertebral fixation element can be clamped between said clamping surface of said T-bar and said tip of said set screw when said set screw is threaded through said first threaded bore into said elongated bore with said tip bearing against the spinal rod.

11. The top-loading clamp of claim 10, wherein said clamping surface of said T-bar is convexly curved to be received within a groove in the vertebral fixation element.

12. The top-loading clamp of claim 10, wherein:

said body includes a bottom surface opposite said top surface and further defines a second threaded bore therethrough from said bottom surface intersecting said elongated bore, whereby said set screw can be threaded alternatively into said first threaded bore or said second threaded bore to clamp said spinal rod within said elongated bore.

13. The top-loading clamp of claim 12, wherein said body is symmetric about a plane including the longitudinal axis of said rod bore.

14. The top-loading clamp of claim 10, wherein said first threaded bore intersects said rod bore at an angle between 60° and 90°.

15. The top-loading clamp of claim 10, further comprising:

a washer having a first surface configured to engage the spinal rod, and an opposite second surface which includes a plurality of radial splines adapted for interdigitating engagement with a radial splines of the vertebral fixation element, said washer further defining an opening therethrough configured to permit insertion of said washer over said T-bar; and means for slidably engaging said washer to said body adjacent said rod bore, wherein said washer is disposed between the vertebral fixation element and the spinal rod and is clamped therebetween when said set screw bears against the spinal rod so that the interdigitating radial splines prevent rotation of the vertebral fixation element about the projection.

16. The spinal fixation system of claim 15, wherein:

said body defines a hub between said rod bore and said projection, said hub having a shape complementary to said opening in said washer to prevent rotation of said washer about said hub when said washer is disposed thereon; and said means for slidably engaging said washer includes means for mounting said washer on said hub to permit sliding of said washer in a direction parallel to the longitudinal axis of said rod bore.

17. The spinal fixation system of claim 16, wherein said means for mounting includes:

at least one staking recess defined in said first surface integral with said opening; and a staked portion of said hub projecting outward therefrom for engagement within said staking recess when said washer is disposed on said hub.

* * * * *

UNITED STATES PATENT AND TRADEMARK OFFICE
CERTIFICATE OF CORRECTION

PATENT NO. : 5,282,801
DATED : February 1, 1994
INVENTOR(S) : Michael C. Sherman It is certified that error appears in the above-indentified patent and that said Letters Patent is hereby corrected as shown below:

The title page, showing the illustrative figure, should be deleted to appear as per the attached title page.

The Drawings Sheet, consisting of Figs 5,6,7,8,9, and 10, should be deleted to be replaced with the Drawings Sheet, consisting of Figs. 5-10, as shown on the attached pages.

In FIG. 5, the reference Nos. 14,16,20, 26, 27 and 28 are missing.

In. FIG. 6, the reference letter R is missing.

In FIG. 8, the reference No. 40 is missing.

Signed and Sealed this

Sixth Day of September, 1994

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,282,801
DATED : February 1, 1994
INVENTOR(S) : Michael C. Sherman It is certified that error appears in the above-indentified patent and that said Letters Patent is hereby corrected as shown below:

In Column 9, line 5, remove "there-"

In Column 9, line 6, remove "through from said top surface and intersecting"

In Column 9, line 7, remove "said elongated bore;"

United States Patent

Sherman

[11] Patent Number: 5,282,801
[45] Date of Patent: Feb. 1, 1994

[54] TOP TIGHTENING CLAMP ASSEMBLY FOR A SPINAL FIXATION SYSTEM

[75] Inventor: Michael C. Sherman, Memphis, Tenn.

[73] Assignee: Danek Medical, Inc., Memphis, Tenn.

[21] Appl. No.: 18,800

[22] Filed: Feb. 17, 1993

[51] Int. Cl.⁵ ............................................... A61F 5/02
[52] U.S. Cl. ............................................ 606/61; 606/73; 623/17
[58] Field of Search .................. 606/60, 61, 72, 73, 606/62, 64; 623/17

[56] References Cited

U.S. PATENT DOCUMENTS

| 4,987,892 | 1/1991 | Krag et al. | 606/61 |
| 5,053,034 | 10/1991 | Olerud | 606/60 |
| 5,122,131 | 1/1992 | Tsou | 606/61 |
| 5,176,678 | 1/1993 | Tsou | 606/60 |
| 5,209,752 | 3/1993 | Ashman et al. | 606/72 |

FOREIGN PATENT DOCUMENTS 2096465 10/1982 United Kingdom ............... 606/61

Primary Examiner—Peter A. Aschenbrenner
Assistant Examiner—Sonya C. Harris
Attorney, Agent, or Firm—Woodard, Emhardt, Naughton, Moriarty & McNett

[57] ABSTRACT

A spinal fixation system is provided for engagement to the spine of a patient between several vertebral levels, which includes an elongated spinal rod configured for placement adjacent the spine. The system includes a number of vertebral fixation elements, each including a vertebra engaging portion and a rod engaging portion formed by a pair of posts extending from the vertebra engaging portion. The vertebral fixation elements are engaged to the spinal rod each by way of a top-loading clamp that permits access directly from the top of the instrumentation site for tightening the system. In particular, the clamp includes a body defining an elongated bore configured to receive the spinal rod therethrough so that the rod can at least initially slide along the length of the bore. A pair of threaded bores extend from opposite top and bottom surfaces of the body, each intersecting the elongated rod bore. The clamp further includes a projection extending from the body terminating in a T-bar arranged generally parallel to the longitudinal axis of the spinal rod. The T-bar includes a clamping surface directed inwardly toward the elongated bore that is configured to engage the pair of posts of the vertebral fixation element. A set screw is provided that is threaded into one of the threaded bore bearing against the spinal rod disposed within the rod bore, so that the set screw clamps the rod and the posts of the vertebral fixation element against the T-bar.

17 Claims, 3 Drawing Sheets